(12) United States Patent
Maschke (10) Patent No.: US 7,755,058 B2
(45) Date of Patent: Jul. 13, 2010

(54) PATIENT TREATMENT USING A HYBRID IMAGING SYSTEM

(75) Inventor: Michael Maschke, Lonnerstadt (DE)

(73) Assignee: Siemens Aktiengesellschaft (DE)

( * ) Notice: Subject to any disclaimer, the term of this patent is extended or adjusted under 35 U.S.C. 154(b) by 37 days.

(21) Appl. No.: 11/862,702

(22) Filed: Sep. 27, 2007

(65) Prior Publication Data

US 2008/0043901 A1 Feb. 21, 2008

Related U.S. Application Data

(63) Continuation-in-part of application No. 11/598,189, filed on Nov. 9, 2006.

(30) Foreign Application Priority Data

Nov. 10, 2005 (DE) .............. 10 2005 053 994

(51) Int. Cl.
*H01L 27/146* (2006.01)
(52) U.S. Cl. ............................ 250/370.09
(58) Field of Classification Search ............ 250/370.09
See application file for complete search history.

(56) References Cited

U.S. PATENT DOCUMENTS

| 5,042,486 | A | 8/1991 | Pfeiler et al. |
| 5,365,926 | A | 11/1994 | Desai |
| 5,638,817 | A | 6/1997 | Morgan et al. |
| 6,205,347 | B1 * | 3/2001 | Morgan et al. ............ 600/407 |
| 6,556,695 | B1 | 4/2003 | Packer et al. |
| 6,923,768 | B2 | 8/2005 | Camus et al. |
| 7,216,383 | B2 | 5/2007 | Heinl et al. |
| 7,332,724 | B2 * | 2/2008 | Hefetz et al. ........... 250/370.06 |
| 2003/0014132 | A1 | 1/2003 | Ohba et al. |
| 2004/0152970 | A1 * | 8/2004 | Hunter et al. ............ 600/424 |

(Continued)

FOREIGN PATENT DOCUMENTS

DE 4436828 3/1996

(Continued)

OTHER PUBLICATIONS

P. Della Bella et al.; "Endocardial Catheter Ablation of Ventricular Tachycardias"; Rhythm 2005-New Treatments in Heart Failure.

(Continued)

*Primary Examiner*—David P Porta
*Assistant Examiner*—Mindy Vu
(74) *Attorney, Agent, or Firm*—Brinks Hofer Gilson & Lione (57) ABSTRACT

A system and method for treating a patient using a hybrid imaging system is provided. For example, first imaging data is acquired from a patient using a first imaging device. The patient is transferred on a support to a second imaging device. The support extends between the first imaging device and the second imaging device. Second imaging data is acquired from the patient using the second imaging device. The second imaging device structurally allows for catheter treatment in the patient during acquisition of the second imaging data. The first imaging data and the second imaging data are superimposed or fused. The patient is treated with a catheter as a function of the superimposed or fused data while acquiring the second imaging data.

17 Claims, 7 Drawing Sheets

U.S. PATENT DOCUMENTS

| | | | |
|---|---|---|---|
| 2005/0049486 A1* | 3/2005 | Urquhart et al. | 600/429 |
| 2007/0005053 A1* | 1/2007 | Dando | 606/41 |
| 2007/0030945 A1 | 2/2007 | Boese et al. | |
| 2007/0100225 A1 | 5/2007 | Maschke | |
| 2007/0102645 A1 | 5/2007 | Maschke | |
| 2008/0171931 A1 | 7/2008 | Maschke | |
| 2008/0281181 A1* | 11/2008 | Manzione et al. | 600/407 |

FOREIGN PATENT DOCUMENTS

| | | |
|---|---|---|
| DE | 10340552 A1 | 3/2005 |
| DE | 102005012700 | 9/2006 |
| DE | 102005016472 | 10/2006 |
| DE | 102005032755 | 1/2007 |
| DE | 102005048853 | 4/2007 |
| DE | 102005053994 | 5/2007 |
| WO | WO 2004/095069 A1 | 11/2004 |
| WO | WO 2005095069 | 10/2005 |

OTHER PUBLICATIONS

Office Action dated Feb. 12, 2009, U.S. Appl. No. 11/598,189.
Office Action dated Sep. 3, 2008, U.S. Appl. No. 11/ 598,189.
Carto XP EP Navigation, Biosense Webster (2005), http://www.jnjgateway.com/home.jhtml?loc=USENG&p.=viewContent&contentld=09008b988008e25c&nodekey=/Prod_Info/Company/Biosense_Webster/Electrophysiology/EP_ Navigation_Systems.
St. Jude Medical, Inc., ICDs, St. Jude Medical, Oct. 2007, http://www.sjm.com/globals/printpageview.aspx?area=html&param1=resources/html/implan . . .
BiosenseWebster, "Carto XP Electroanatomical Navigation System," BiosenseWebster, Inc. 2004, Order No. B0037, Printed in USA 0404007.5.

* cited by examiner

PATENT TREATMENT USING A HYBRID IMAGING SYSTEM

CLAIM OF PRIORITY

This application is a continuation-in-part application of and claims the benefit of the U.S. application Ser. No. 11/598,189 filed on Nov. 9, 2006, which is hereby incorporated by reference. The U.S. application Ser. No. 11/598,189 claims the benefit of the German application No. 10 2005 053 994.7 filed on Nov. 10, 2005, which is hereby incorporated by reference.

BACKGROUND

The present embodiments relate to medical imaging. In particular, a system and method of treating a patient using a hybrid imaging system is provided.

Diagnosis devices for combined and/or combinable radiographic and nuclear medical examinations and digital imaging methods have now become common practice in medical diagnostics. Methods of this type have been used for some time, e.g. in computer tomography, for magnetic resonance examinations, ultrasound examinations and for nuclear medical methods.

However, accuracy of combined examinations may be compromised because of patient positioning. For example, moving the positioning of a patient from one imaging modality to another imaging modality can disturb data correlation and/or comparison. Also, it may be difficult to perform invasive treatment on a patient during imaging due to the physical nature of the imaging system.

BRIEF SUMMARY

By way of introduction, the preferred embodiments described below include a hybrid imaging system, a catheter system, and methods of treating a patient. At least two imaging modalities are used to create superimposed images. Catheter treatment is performed on the patient as a function of the superimposed images.

According to a first aspect, a method for treating a patient using a hybrid imaging system is provided. First imaging data is acquired from a patient using a first imaging device. The patient is transferred on a support to a second imaging device. The support extends between the first imaging device and the second imaging device. Second imaging data is acquired from the patient using the second imaging device. The second imaging device structurally allows for catheter treatment in the patient during acquisition of the second imaging data. The first imaging data and the second imaging data are superimposed or fused. The patient is treated with a catheter as a function of the superimposed or fused data while acquiring the second imaging data.

According to a second aspect, a computer-readable medium has stored therein instructions executable by a processor. The instructions comprise acquiring first imaging data from a patient using a nuclear medicine imager. The patient is transferred on an automated support to a non-encapsulating imager. The automated support is extendable between the nuclear medicine imager and the non-encapsulating imager. Second imaging data is acquired from the patient using the non-encapsulating imager. The first imaging data and the second imaging data are superimposed or fused substantially at the same time as acquiring the second imaging data.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The embodiments propose a diagnosis device for increasing accessibility to a patient. To this end, a diagnosis device is proposed for combined and/or combinable radiographic and nuclear medical examinations with an x-ray source, with an examination room for accommodating a patient, with a gamma radiation source arranged in the body, with the diagnosis device being designed in order to carry out the radiographic examination by evaluating the measurement of the x-rays, and in order to carry out a single photon emission (SPE) examination as a nuclear medical examination by evaluating the gamma radiation, with a detector system that has a detector surface for simultaneously measuring the x-ray and gamma radiation without changing the patient's position and/or which is designed to record a two-dimensional locally-resolved and object-imaging individual x-ray projection image.

Diagnosis devices known as SPECT (Single Photon Emission Computer Tomographs) that enable a functional imaging have been implemented over the last few years in the field of nuclear medicine. The method is based on the basis of a tracer-principle with radioactive substances. In this method, by adding a very small quantity of a radioactive marked compound into the object to be examined, the metabolism thereof is monitored by measuring the radioactive radiation from the outside, in other words in a non-invasive manner. The marked tracer accumulates in specific organs and/or tumors, scar tissue, or metastases and thus permits a good diagnosis of the metabolism, the locating of tumors, scar tissue, and metastases or also an evaluation of the perfusion of the myocardial muscle. With the SPECT, radionuclides (isotope) are used, that decay while emitting individual gamma quanta. Tracers used in SPECT are for instance Tc99m-MDP (Tc=Technetium) for bones, Tl-201 or Tc99m-MIBI for Myocardial Perfusion or Iodine-131 in the case of thyroid tumors. Nuclear medical imaging uses the tracer principle by producing images of the distribution of the radioactivity of a tracer. The radioactive radiation is usually detected by way of scintillation detectors. Similarly, positron emission tomography ("PET") may be utilized to obtain similar results.

As is known, the SPECT and PET techniques do not provide good anatomical imaging, thereby rendering the localization of detected tumors, scar tissue or metastases in the body of the patient problematic for instance. To achieve a better anatomical imaging, the patient can be examined before or after the SPECT or PET examination using radiographic CT (Computed tomographs) or MRI (Magnetic Resonance imaging). The challenge which then presents itself is that of correct registration, namely to correctly overlay and jointly display the recordings of the SPECT or PET and the CT and/or MRI. To this end, the image data is transferred to a common coordinates system. The disadvantage of these types of registration methods is that they have to be carried out interactively after the examinations and they are restricted in their accuracy.

The SPECT (Single Photon Emission Computer Tomography) CT diagnosis device of the applicant Siemens A G, Erlangen, Germany, with the product name "Symbia," provides the opportunity of carrying out nuclear medical SPECT examinations and radiographic CT examinations consecutively, but nevertheless in a combined piece of equipment.

A detector element is used for the combined detection of x-rays and gamma radiation. This detector element has a converter, which generates a charge signal as a function of incident x-ray or gamma quanta. In an evaluation device which is arranged downstream, the charge signal is amplified and evaluated on two different branches, with the first branch comprising an individual pulse analyzer in order to determine information for PET (Positron Emission Tomography) and the second branch comprising a pulse sequence analyzer in order to determine information for CT (computer tomography).

For PET, the detectors are positioned in rings surrounding the patient. The detectors are fixed and may not move. Usually, a PET scanner may not have a collimator. A SPECT scanner has detectors in two detector heads, which are opposite to each other or in a defined angle, e.g. 90 degrees. The SPECT detectors have a collimator to achieve orientation in 3D space.

The diagnosis device is designed for a combined and/or combinable radiographic and nuclear medical examination, with the radiographic examination being designed in particular as an x-ray projection examination. The evaluations of both the radiographic and also the nuclear medical examinations preferably comprise digital imaging methods.

The diagnosis device comprises an x-ray source, which generates x-rays of the human body for examination purposes. The x-ray source is preferably designed as an x-ray tube, preferably having x-ray voltages from 120 to 150 kV, which, in particular, produce x-ray quanta with energy of approximately 100 keV.

Furthermore, an examination room is provided, which serves to accommodate a patient. For the nuclear medical examination and prior to the start of the examination, radioactive materials (tracers) are placed in the patient's body in the tissue/organ to be examined, with the aid of suitable radiopharmaceuticals. These radiopharmaceuticals and/or radioactive materials emit gamma radiation (high energy photons). The radiopharmaceuticals mentioned in the introduction are typically used.

The energies of the x-ray quanta of the x-ray source and the energies of the gamma quanta preferably lie in a similar energy range, in particular from 80 to 160 keV and are thus of a physically similar nature. For distinction purposes, the expressions x-rays, x-ray quanta etc. within this application nevertheless relate to photons, which are generated in the x-ray source and the expressions gamma radiation, gamma quanta etc. relate to photons that are emitted by radioactive materials (tracers) placed within the body of the patient.

On the one hand, the diagnosis device is designed to carry out a classical radiographic examination, in other words an x-ray projection medical examination on the patient. On the other hand, the diagnosis device is designed to carry out a SPECT or PET examination on the patient. In the case of the SPECT or PET examination known per se, the gamma quanta emitted by the radioactive materials arranged in the body of the patient is detected in an integrating measurement.

The diagnosis device comprises a detector system. The x-ray and gamma quanta can be detected using one and the same detector system, in particular using one and the same detector elements. The detector system preferably comprises a flat detection surface and/or a detection surface which is only slightly curved having a radius of curvature greater than the multiple, in particular greater than the threefold distance of the detection system from the central point of the examination room, with the measurement space of the detector system especially only penetrating the examination room without overlapping. In particular, the detection system does not have a detector arrangement, which is suitable for a PET (positron emission tomography) examination.

With the second alternative embodiment, a provision is made that the detector system or a detector system for the radiographic examination is designed to record a two-dimensional locally-resolved and graphically imaging individual x-ray projection image. In contrast with the known CT devices, which have a detector array with one or a number of column sensors, the detector system has a flat panel detector for instance, which allows a two-dimensional recording.

The idea underlying the embodiments is to reduce the system-specific space required for the diagnosis device by adjusting the system technology. A first alternative embodiment is provided to reduce the space requirement by economizing on detectors. With the second alternative, an examination based on x-ray projection images is carried out in place of the radiographic CT, thereby in this way particularly saving on the bulky annular construction (gantry) used for recording and on the rapid rotation of the detector and the x-ray source about the patient. Both alternatives are thus advantageous in that the patient is more easily accessible during the examination. The basis is thus established not only to examine but also to treat the patient in the diagnosis device.

In addition, it is advantageous that the diagnosis device contains all necessary elements of an SPECT or PET device and an x-ray device, but however also makes joint use of a plurality of components, such as an image computer, an image and data storage device, a DICOM data network interface, a patient table for instance, thus rendering it more cost-effective compared with two individual devices.

Furthermore, the first alternative embodiment is additionally advantageous in that the radiographic and the nuclear medical examination is carried out at the same position without changing the patient's position and a common measurement coordinates system is thus used.

The detector system is preferably designed as a flat panel detector with a sensor matrix and/or a pixel matrix and/or comprises the above. Provision is made in particular for several sensors/pixels to be assigned to a common readout channel and/or a common analog/digital converter.

In a preferred embodiment, the flat panel detector features a readout matrix, in particular a TFT matrix, upstream of which is arranged a converter, which converts an incident high-energy photon, i.e. an x-ray or a gamma quanta, into an electrical charge or into a lower-energy light pulse. The converter is designed particularly as a scintillator.

In order to be able to avoid artifacts and mismeasurements, an optional collimator can be provided in particular as a scattered radiation filter. The collimator is designed as a directional filter for the high-energy photons, i.e. the x-ray and gamma quanta. Photons comprising a movement direction that is vertical or essentially vertical to a detector surface and/or to the converter are preferably admitted by the collimator.

A signal for each individual sensor and/or for each individual pixel can be advantageously output by the flat panel detector by means of an adjustable or controllable integration time, with the individual sensors and/or individual pixels being configured in particular as integrating elements.

In one possible embodiment, the diagnosis device features an SPECT or PET detector in a sequential arrangement and in particular a separate x-ray detector. Provision is preferably made for a patient table to be able to be introduced from the SPECT or PET detector side as well as from the x-ray detector side.

In one preferred embodiment, the diagnosis device is designed to produce 3D soft tissue images by evaluating the detected x-ray radiation. The diagnosis device is preferably designed as a sequential combination of SPECT or PET detector and x-ray detector, with the SPECT detector being integrated into an angiographic x-ray diagnostics device for rotational angiography. In principle, the embodiments are based on the idea of combining anatomical imaging (radiography) with functional diagnostic (SPECT or PET). The last-mentioned embodiment additionally provides for at least partially carrying out the functional diagnostics by radiography. This method results in a dual identification of soft parts, in particular of metastases, scar tissue, or tumors, so that the registration can be examined in a simple manner.

A control and evaluation device is expediently provided, which supports different operation modes, namely in particular the insulated and/or combined and/or combinable use of SPECT, PET or x-ray examination possibilities. In particular, a module for the data fusion or superimposition of radiographic and nuclear medical measurement data is provided, which results in combined SPECT or PET x-ray data sets. The data fusion or superimposition is preferably carried out in real-time.

With a preferred embodiment, the diagnosis device comprises an integrated tumor or scar tissue treatment device and/or a device for minimally invasive patient treatment, which is and/or are coupled for control purposes to the control and evaluation device. The tumor or scar tissue treatment device is a laser ablation device. Alternatively, the tumor or scar tissue treatment device is a radio frequency ablation device. Alternatively, the tumor or scar tissue treatment device is a cryoablation device.

A movement sensor system is optionally provided to capture patient movements in the diagnosis device. The patient movements are recorded during the examination and/or during a transition period from a nuclear medical examination to the radiographic examination and are considered when fusing or superimposing the measurement results. The control and evaluation device is a module, which is designed to control the movement sensor system as well as to correct the nuclear medical and/or radiographic measurement data on the basis of the measured patient movements. The following embodiments are possible:

Movement sensor system with a mathematical movement sensor, which derives the patient movements from the image signals, in particular the measurement signals of the nuclear medical and/or radiographic examination.

Movement sensor system with a sensor having an electrical operation principle.

Movement sensor system with a capacitive operation principle.

Movement sensor system with a magnetic operation principle.

Movement sensor system with an acoustic operation principle.

Movement sensor system with an optical operation principle, e.g. by scanning using a laser beam or using an optical camera operating (in particular in the visible range) or in the infrared range.

The data of the movement sensor system is either transmitted to the control and evaluation device with a fixed link or wirelessly.

With a particularly preferred embodiment, the movement sensor system is designed in RFID transponder technology, and is equipped in particular with an RFID receiver system. Provision is preferably made for the RFID transmitter to be equipped with an adhesive surface and affixed to the patient in a manner similar to that of an adhesive patch. In particular, the RFID transmitter is designed as a disposable article, which is disposed of after its use.

Optional sensors for measuring the ECG, breathing and vascular pulsation are provided to detect organ movements, such as for instance movements of the heart, the ribcage and the blood vessels. The measurement results are preferably forwarded to the control and evaluation device and taken into account with the image reconstruction and/or data fusion, and artifacts emanating therefrom are especially eliminated for instance by "gating."

A chest band can be used for instance to eliminate breathing artifacts, said chest band comprising sensors that are designed to record the breathing amplitude and/or frequency. Another option is to calculate the breathing amplitude and/or frequency from the ECG signal, in particular from an envelope curve of the ECG signal. In addition or alternatively, the pulse of the vessel is determined by evaluating the ECG or the blood pressure curve.

An advance system is preferably provided to move the patient through the measurement area of the detector system. The advance system allows the patient to be advanced through the diagnosis device. In particular, the diagnosis device is designed to control the advance system and detector system in a synchronized manner.

With one development, the advance system comprises a position sensor which is designed to record the advance movement of the patient and is arranged for instance in a moveable examination table. The data of the position sensor, in particular the movement data of the patient and/or of the examination table, is preferably forwarded to the evaluation and control device and taken into account during the image reconstruction and/or data fusion or superimposition.

With a preferred embodiment of the diagnosis device, a calibration module is preferably provided in the evaluation and control device, with the movement sensor system and/or the position sensor being calibrated in respect of the spatial coordinates of the diagnosis device.

It is advantageous if x-ray source and/or detector system are arranged opposite one another on the end segments of a C-arm or U-arm shaped bracket, which is rotatable such that the end segments describe circular paths about the patient arranged in the central point of the circular path. With one possible embodiment, the C-arm or U-arm construction is accommodated by an industrial robot, preferably having four to six degrees of freedom, such as, for example, five degrees of freedom. Alternatively, the x-ray source and detector system can be mounted on moveable stands, which are mounted for instance on the ceiling or the floor of a frame or of a treatment room, with the stands preferably being moveable in three degrees of freedom.

With an advantageous development, the diagnosis device, in particular the evaluation and control device, is designed such that measurement data of the nuclear medical examination and the radiographic examination is temporarily offset, and/or can be read out and/or is read out alternately from the detector system and/or the detectors. In particular, the readout process is clocked and/or synchronized using the controller of the x-ray source. In a diagnosis device with separate nuclear medical and radiographic detectors, this embodiment allows the patient to be moved without interruption from the SPECT or PET scanner segment into the x-ray segment or vice versa.

Radiation protection curtains or covers are preferably arranged on the diagnosis device in order to protect the operating personnel.

It should be noted that the described embodiment of the diagnosis device with a tumor or scar tissue treatment device is preferable, nevertheless other embodiments of apparatus for therapies, which require anatomical and functional imaging at the same time as easy patient accessibility, are likewise possible. By way of example, a perfusion of the myocardial muscle can be determined by way of the nuclear examination and an anatomical assignment can be carried out at the same time by way of the radiographic examination of the corresponding coronary vessels, and a corresponding balloon dilation is derived therefrom and a stent or stem cells are introduced. With these applications, the diagnosis device is designed with the appropriate apparatus to implement the treatment.

The advantages achieved with the embodiments thus particularly consist in the good anatomical imaging by the radiographic examination, combined with the functional imaging with the display of the metabolism by the nuclear medical examination that can be fused or superimposed in a short amount of time. Also, a good accessibility to the patient is provided for tumor or scar tissue therapy.

Figure 1:
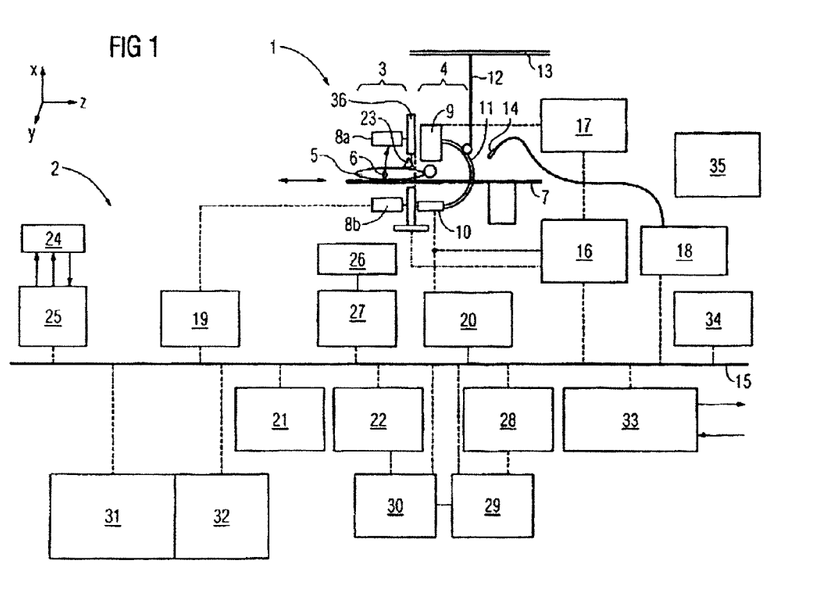
FIG. 1 shows a schematic representation of a first exemplary embodiment of an inventive diagnosis device.

FIG. 1 shows a schematic representation of a first exemplary embodiment of a diagnosis device or hybrid imaging system 1 with the block diagram structure of an evaluation and/control device 2.

The diagnosis device 1 comprises a first measurement area or imaging device 3 for recording SPECT images and a second measurement area 4 for recording x-ray images. Alternatively, the first measurement area or imaging device 3 is for recording PET images. A patient 5 administered with radiopharmaceuticals containing radioactive materials prior to the examination. Because scar tissue is basically dead tissue, it does not have a good metabolism. However the surrounding living tissue, such as heart tissue, where the tracer is accumulated does have a good metabolism. Therefore, the scar tissue has a good visibility compared to the living tissue.

The support 7 is a flat bed or platform for moving the patient 5 between the first imaging device 3 and the second imaging device 4 without changing a resting position of the patient 5. The support 7 can be moved in the Z-direction in an automated process, for an examination, firstly through the first measurement area 3 and then through or into the second measurement area 4. For example, the support 7 consists of a conveyor belt, a platform that is operable to move upon supporting rails, or any other known or future conveying technique or system. The support 7 is extendable between the first imaging device 3 and the second imaging device 4 and may be attached to or separate from the imaging devices 3 and/or 4.

The first measurement area or imaging device 3 comprises a SPECT measuring head or imager. The imaging device 3 in FIG. 1 has two opposing detector arrays 8a, b that are aligned to one another. The detector arrays 8a, b each include a collimator (not shown in further detail), which operates as a directional filter and/or as a scattered radiation filter for gamma radiation emitted from the tracer. The detector arrays 8a, b have a plurality of quanta detectors, which are semiconductor detectors or photo multipliers having scintillation and/or converter layers arranged upstream thereof. Alternatively, the imaging device 3 is a PET measuring head or imager. For example, the structure and functionality of the PET system disclosed in the United States Patent Publication U.S. 2007/0100225 A1, which is hereby incorporated by reference, is utilized. By using a SPECT or PET imager, high costs of MRI as well as the effects of strong magnetic fields on other components can be avoided. Also, MRI may not provide functional image data, such as electrophysiological activity, as good as a SPECT or PET imager. Any other known or future nuclear medicine measuring head or imager may also be utilized.

The second measurement area or imaging device 5 has a radiation source 9 in the form of an x-ray source as well as an x-ray detector 10 for detecting x-rays emitted by the x-ray source 9. The radiation source 9 and the x-ray detector 10 are arranged on the free end segments of a C-arm or U-arm 11, which is linked to a frame 13 in a moveable manner by way of a stand 12. By rotating the C-arm or U-arm 11, the x-ray source 9 and the x-ray detector 10 can be guided around the reclining patient 5 in a circular path. Alternatively, the C-arm or U-arm 11 is controlled or moved by a robot unit 200 (see FIG. 2). The robot unit 200 is mounted on the floor, wall, or ceiling and is operable to move about on either surface.

The second measurement area or imaging device 5 may be any known or future imaging device that structurally allows for catheter treatment in the patient during image acquisition. For example, the second measurement area or imaging device 5 is a non-encapsulating imager.

Furthermore, an ablation catheter 14 is provided. The ablation catheter 14 can be inserted into the patient reclining in the diagnosis device 1 for treatment purposes. For example, the ablation catheter 14 is used for tachycardia treatment. Scar tissue may form on or in the heart due to a heart attack or other medical reasons. Close to the scar tissue, areas of unwanted electrical current channels are generated. These channels cause the heart muscle to "misfire," which may result in a very fast beating of the heart, known as tachycardia. The ablation catheter 14 is used to remove, cut, or interrupt the unwanted electrical channels close to the scar tissue to prevent misfiring of the heart. The ablation catheter 14 is a laser, RF, heat, cryogenic, or any other known or future ablation catheter. Alternatively, the ablation catheter also includes catheter localization and/or imaging features, such as an ultrasound catheter.

The evaluation and control device 2 is connected to a plurality of modules via a data bus 15. The data bus 15 is connected to a system controller 16, which comprises a first output for controlling the x-ray detector 10, a second output for controlling the detector array 8a, b, and a third output for controlling a high voltage generator 17 for supplying the x-ray source 9. The data bus 15 is also connected to an ablation device 18, which controls the ablation catheter 14. The ablation device 18 may be manipulated by a medical professional or a robot unit.

Starting from the detector arrays 8a, b, a further signal path leads to the data bus 15 via an SPECT or PET preprocessing module 19. A corresponding signal path likewise leads from the x-ray detector 10 to the data bus 15 via an x-ray and preprocessing module. The data bus 15 is connected to an image processing unit for SPECT or PET images 21 and to an image processing unit for x-ray images 22. The data processing for soft tissue x-ray images (DynaCT) is also carried out in the latter.

A movement sensor system 23 is provided on the diagnosis device 1 to record patient movements during the examination, said movement sensor system 23 being linked to the data bus 15 by way of an interface 24 and a movement and gating processor 25. Furthermore, physiological sensors can be attached to the patient 5, said sensors supplying signal data in a module for physiological signal processing 27 by way of an interface 26. In particular, electrocardiogram ("ECG"), pulse, respiration and blood pressure data is received and further processed in the module 27. For example, an ECG system is used to gate the imaging of the second measurement area or imaging device 5 to compensate for heart movement. The results of the signal processing and/or the signal data are fed into the data bus 15 by the module 27.

In an image fusion or superimposition and reconstruction unit 28, the SPECT or PET data and the x-ray images/soft tissue x-ray images are merged and transferred in a combined display. An image correction unit 29 is provided to compensate for patient movements and physiological changes in the patient during the examination. In addition, a calibration unit 30 is integrated in the evaluation and control device 2.

The results of the examination are displayed in a display unit 31, on which the SPECT or PET x-ray images or combined images can be displayed on a monitor for instance. Furthermore, operating and control data can be displayed for the diagnosis device 1, in particular for the ablation device 18. A human-machine interface 32 serves to manually control the diagnosis device 1, in particular the SPECT or PET, the x-ray system and the ablation device 18. Alternatively, some or all of the control of the diagnosis device 1 may be automated or accomplished by a robot unit. A DICOM interface 33 for communicating with a network for transmitting patient data and image data as well as an image and data storage device 34 are provided for further processing and documentation of the examination results and of the treatment process. The diagnosis device 1 also comprises voltage supply units 35 for supplying the individual modules.

The diagnosis device 1 may comprise fewer or more components. For example, catheter localization or mapping systems are integrated with or used in addition with the imaging devices for quality control. Also, separate imaging catheters, such as ultrasound catheters, may be used for additional imaging during treatment procedures.

Typical examination protocols and/or workflows for the diagnosis device 1 in FIG. 1 are specified below:

Workflow 1:
Tracer injection into the patient 5;
Optional x-ray contrast agent injection into the patient 5;
X-ray examination (preferably soft tissue x-ray examination); and
SPECT or PET examination (e.g. of the whole body)

Workflow 2:
Tracer injection into the patient 5;
Optional x-ray contrast agent injection into the patient 5;
SPECT or PET examination (e.g. of the whole body); and
X-ray examination (preferably soft-tissue x-ray examination, in particular in an organ region determined by the SPECT or PET examination as affected).

Workflow 3 with minimally invasive therapy:
Tracer injection into the patient 5;
Optional x-ray contrast agent injection into the patient 5;
SPECT or PET examination (e.g. of the whole body);
X-ray examination (preferably soft-tissue x-ray examination, in particular in the organ region determined by the SPECT or PET examination as affected);
Insertion of the ablation catheter 14 using x-ray control;
Ablation of the tumor or scar tissue-border; and
Monitoring the ablation using x-ray recordings.

Workflow 4 with high-resolution pre-recordings and with minimally invasive therapy:
High-resolution pre-recordings using CT or MRI (sent and/or received by way of the DICOM interface);
Repositioning the patient 5 in the diagnosis device 1;
Tracer injection into the patient 5;
Optional x-ray contrast agent injection into the patient 5;
SPECT or PET examination (e.g. of the whole body);
"Software based registration" and fusion of the 3D pre-recordings (CT, MRI) with the SPECT or PET recordings;
X-ray examination (preferably soft tissue x-ray examination in particular in the organ region determined by the SPECT or PET examination as affected), with a minimal resolution but more up-to-date data than the prerecording;
Insertion of the ablation catheter 14 using x-ray control;
Ablation of the tumor or scar tissue-border; and
Monitoring the ablation using x-ray recordings.

Figure 2:
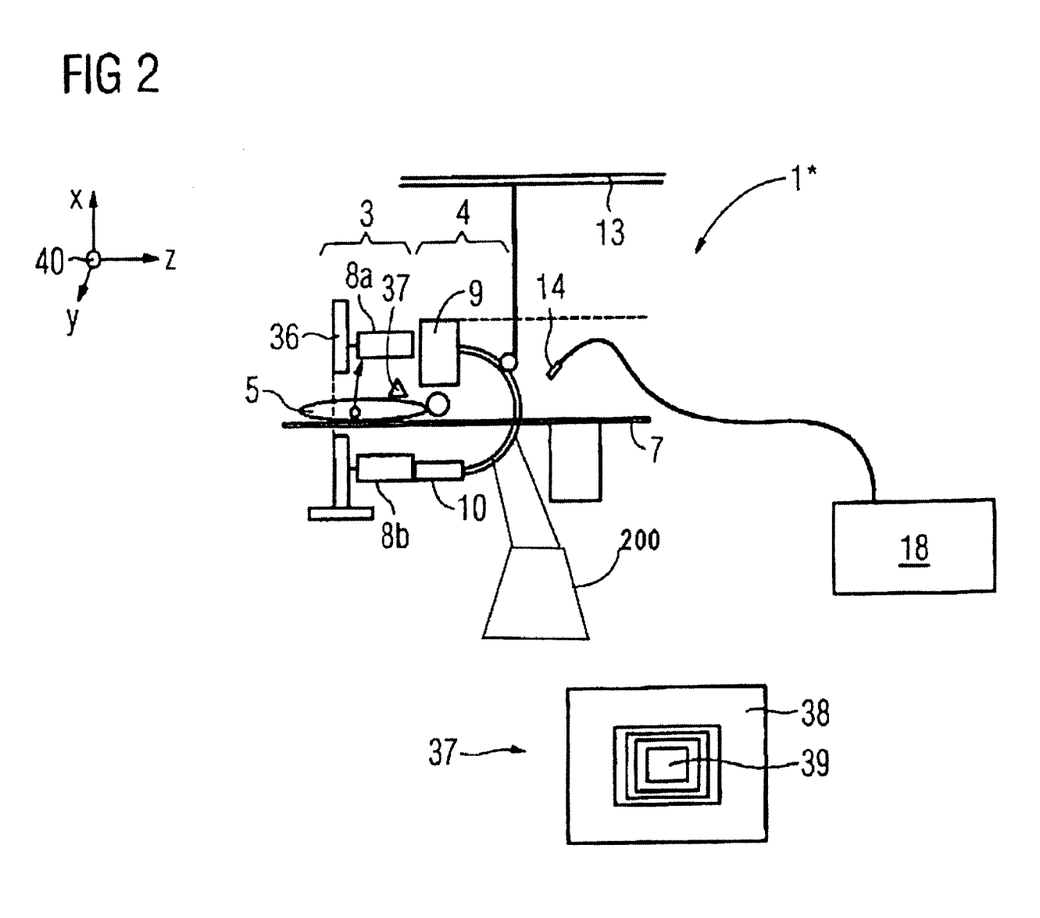
FIG. 2 shows a block diagram of a second exemplary embodiment of an inventive diagnosis device.

The upper region of FIG. 2 shows a modified embodiment of the diagnosis device 1 in FIG. 1. The diagnosis device 1\* in FIG. 2 has a diaphragm 36, which, in contrast to the embodiment in FIG. 1, is arranged in front of the detector arrays 8a, b and the x-ray source 9 and the x-ray detector 10 arranged downstream thereof. With the diagnosis device 1\*, both the first and also the second measurement area or imaging devices 3 and/or 4 are located on a common side of the diaphragm 36. An RFID transponder adhesive patch 37 is affixed to the patient 5. The RFID transponder adhesive patch 37 is an adhesive patch 38 and/or a carrier material that can be affixed to human skin and the actual RFID transponder 39 in accordance with the magnification in the lower region of FIG. 2. An RFID position sensor receiver 40 is provided to pinpoint the RFID transponder adhesive patch 37 and thus also the precise position and movement of the patient 5, which feeds its measurement values into the data bus 15. FIG. 2 also shows a robot unit 200. The robot unit 200 is used to control various aspects of the second measurement area 4, such as a C-arm or U-arm. The robot unit 200 is mounted on the floor, wall, or ceiling and is operable to move about on either surface.

Figure 3:
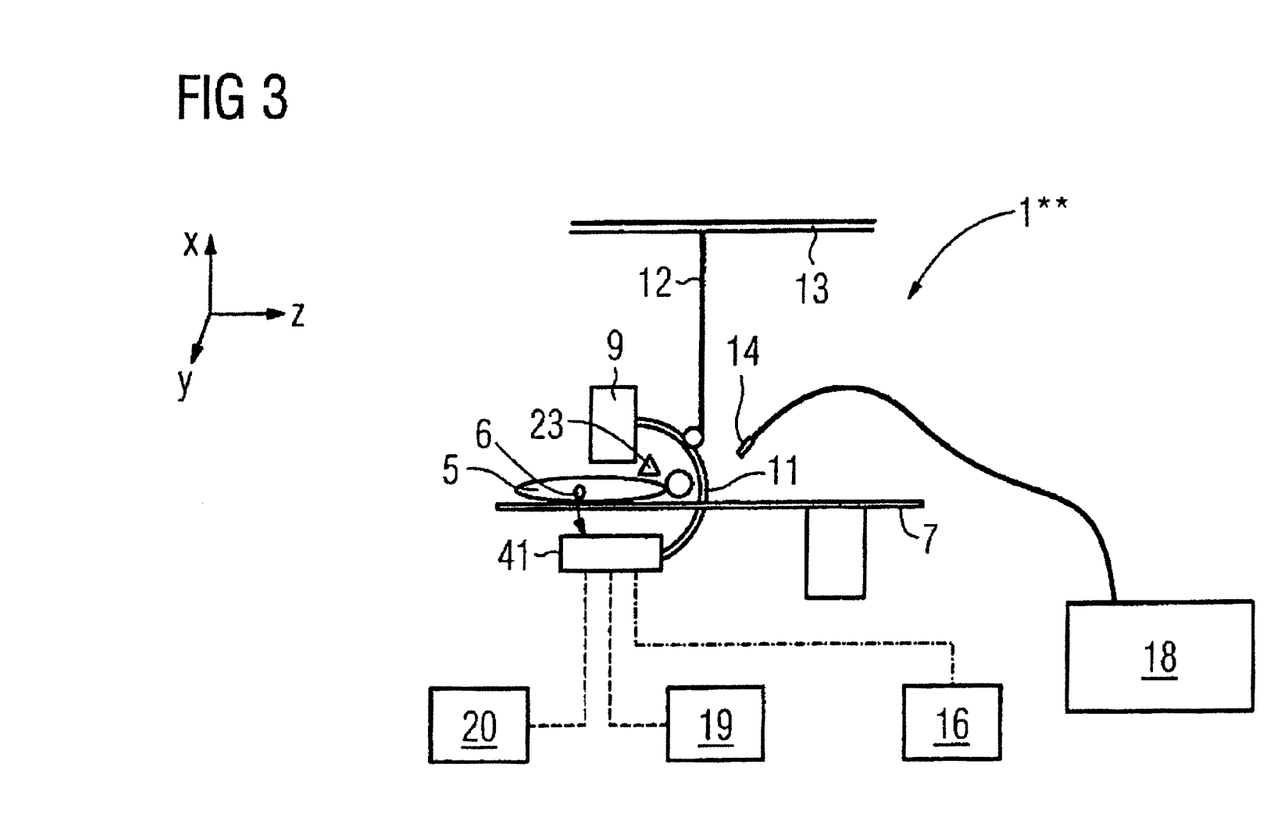
FIG. 3 shows a schematic representation of a third exemplary embodiment of an inventive diagnosis device.

FIG. 3 shows a third embodiment of a diagnosis device **1\*\*, which differs from the diagnosis device 1 in FIG. 1 in that the functions of the detector arrays 8a, b (FIG. 1) and the x-ray detector 9 (FIG. 1) are combined in a common detector 41. The detector 41 can register both the x-rays emanating from the x-ray source 9 and also the gamma radiation emanating from the tracer 6 and can thus carry out a simultaneous measurement using both radiation types without changing the patient's position. The detector 41 is preferably designed as a solid body detector, in particular with a flat or essentially flat or only slightly curved detector surface. In the diagnosis device 1\*\* in FIG. 3, the first and second measurement areas or imaging devices 3 and/or 4 of the diagnosis device 1 in FIG. 1** are designed to overlap and/or to be congruent.

Figure 4:
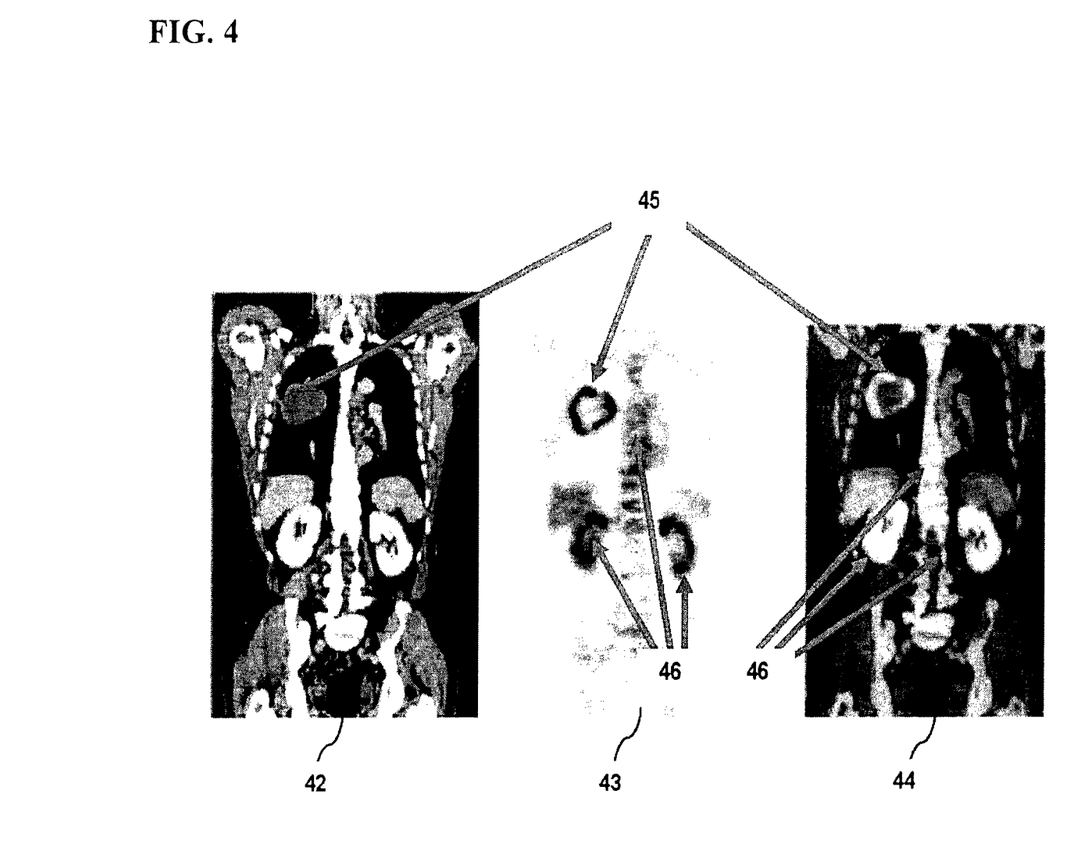
FIG. 4 shows an exemplary embodiment of a data fusion of an x-ray image having a SPECT recording.

FIG. 4 illustrates the fusion or superimposition of measurement data of a SPECT or PET examination and an x-ray examination. A 2D cross-section of a 3D x-ray soft part image 42 is shown in the left side in FIG. 4 and a SPECT recording 43 of the same region in the body of the patient 5 is shown in the center. These two recordings 42 und 43 are produced using a diagnosis device according to FIG. 1, 2 or 3. A combined SPECT/x-ray soft part image 44 is shown on the right side. The image 44 includes the merged measurement data of recordings 42 and 43. The combination, fusion, or superimposition of the measurement data results in a combined image 44, in which primary lung tumors 45 and secondary tumors and metastases 46 can be better and more clearly detected by the treating physicians than in the non-merged images 42 and/or 43. Alternatively, scar tissue, such as scar tissue in the heart resulting from a tachycardia, can be clearly detected rather than lung tumors.

Figure 5:
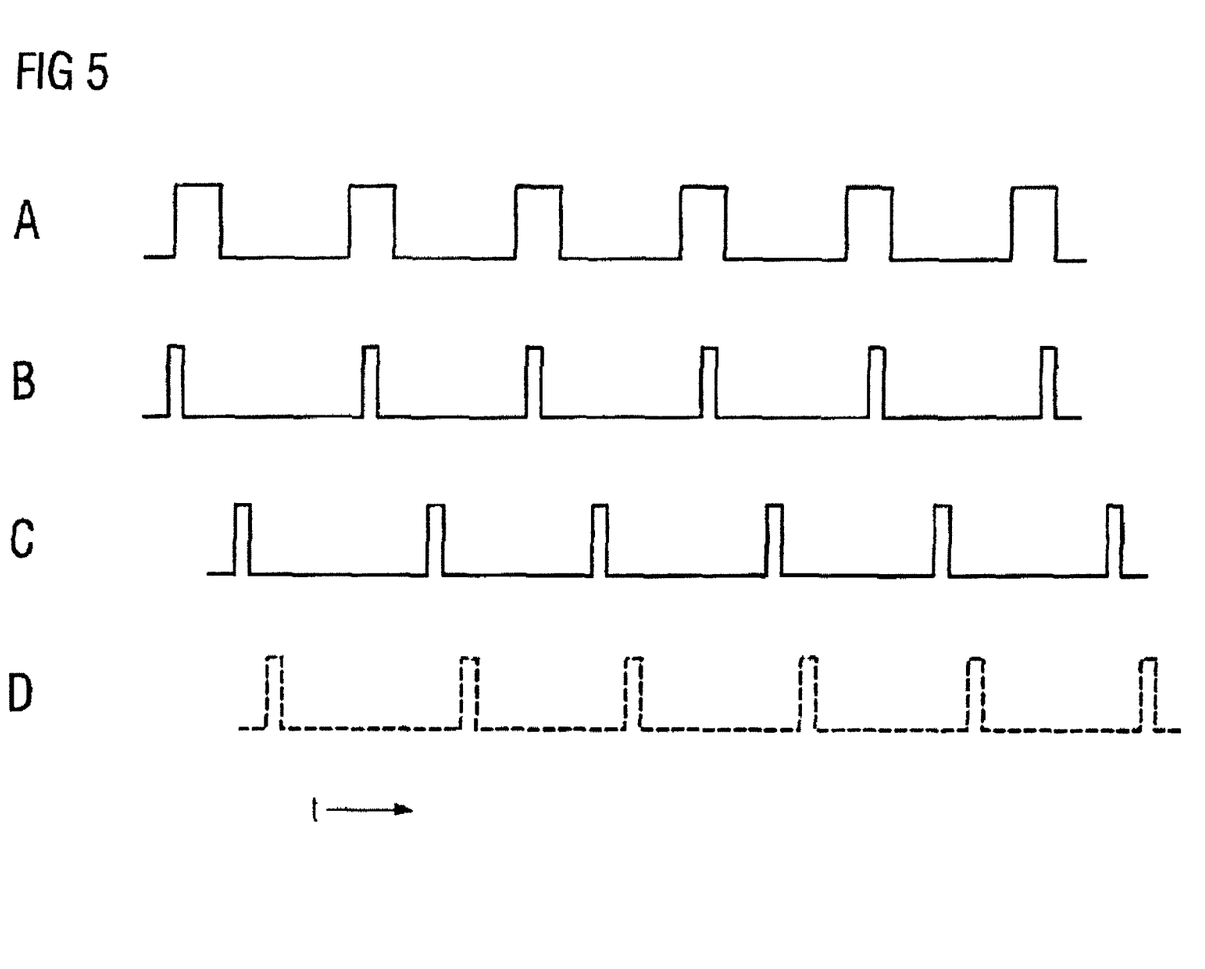
FIG. 5 shows a schematic representation of signal paths to illustrate a clocked readout of a detector system of the exemplary embodiments 1 or 2 of FIG. 1.

FIG. 5 illustrates a clocked readout of the different sensors in the diagnosis device 1, 1\* or **1\*\* of FIGS. 1, 2 and/or 3. In the first row, the signal path A for reading out the quanta detectors of the detector arrays 8***a, b* over time is shown, with the quanta detectors being read out at a high signal level. In the second row, the signal path B for reading out the ECG and the respiration is shown. The third row shows the signal path C for outputting an x-ray pulse by the radiation source 9. A comparison of the signal paths A and B shows how the radiation source 9 is only activated at times at which the quanta detectors are not read out. In this way, mismeasurements by the quanta detectors are avoided. The signal path D relates to the temporal curve of the readout of the x-ray detector 10, which is read out in each instance following an x-ray pulse. The quanta detectors and x-ray detectors are read out alternately and in a non-overlapping fashion. The detector 41 in FIG. 3 can also be controlled in a similar manner, with measurement data relating to the gamma radiation and measurement data relating to the x-rays being read out alternately.

Figure 6:
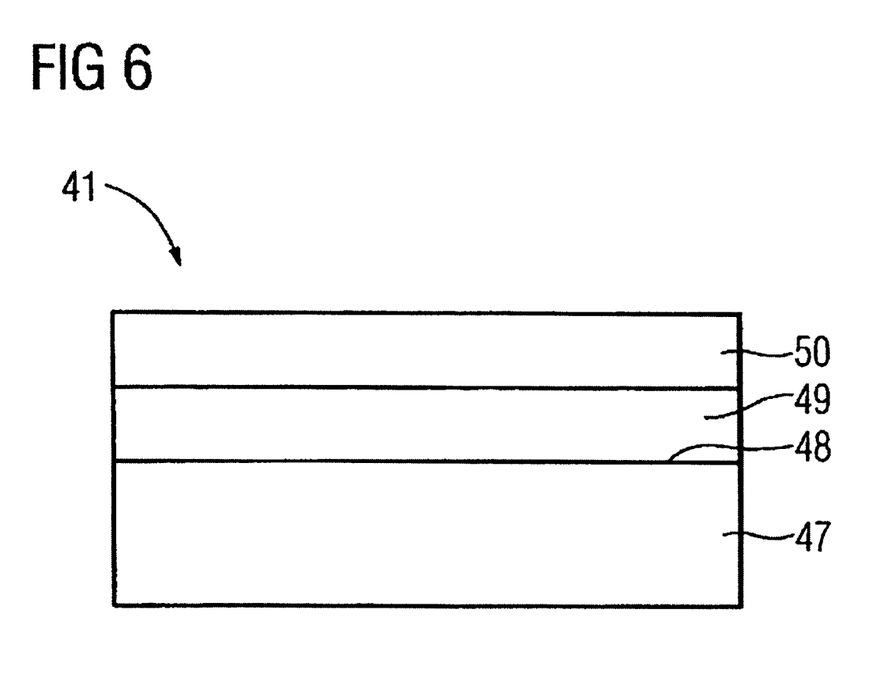
FIG. 6 shows a schematic representation of a detector in FIG. 3.

FIG. 6 shows a schematic representation of the detector 41 in FIG. 3. The detector 41 comprises a sensor matrix or pixel matrix 47 in which are arranged a plurality of individual sensors or pixels in rows and columns. The top side of the sensor matrix or pixel matrix 47 forms the detector surface 48 that is hit by the photons or positrons to be measured. Upstream of the sensor matrix or pixel matrix 47 is arranged a converter 49, which converts the high-energy photons or positrons, i.e. x-ray quanta or gamma quanta, into low-energy light pulses or electrical charges. A collimator 50 is optionally arranged upstream of the converter 49. The collimator operates as a directional filter or a scattered radiation filter for the incident high-energy photons or positrons.

Figure 7:
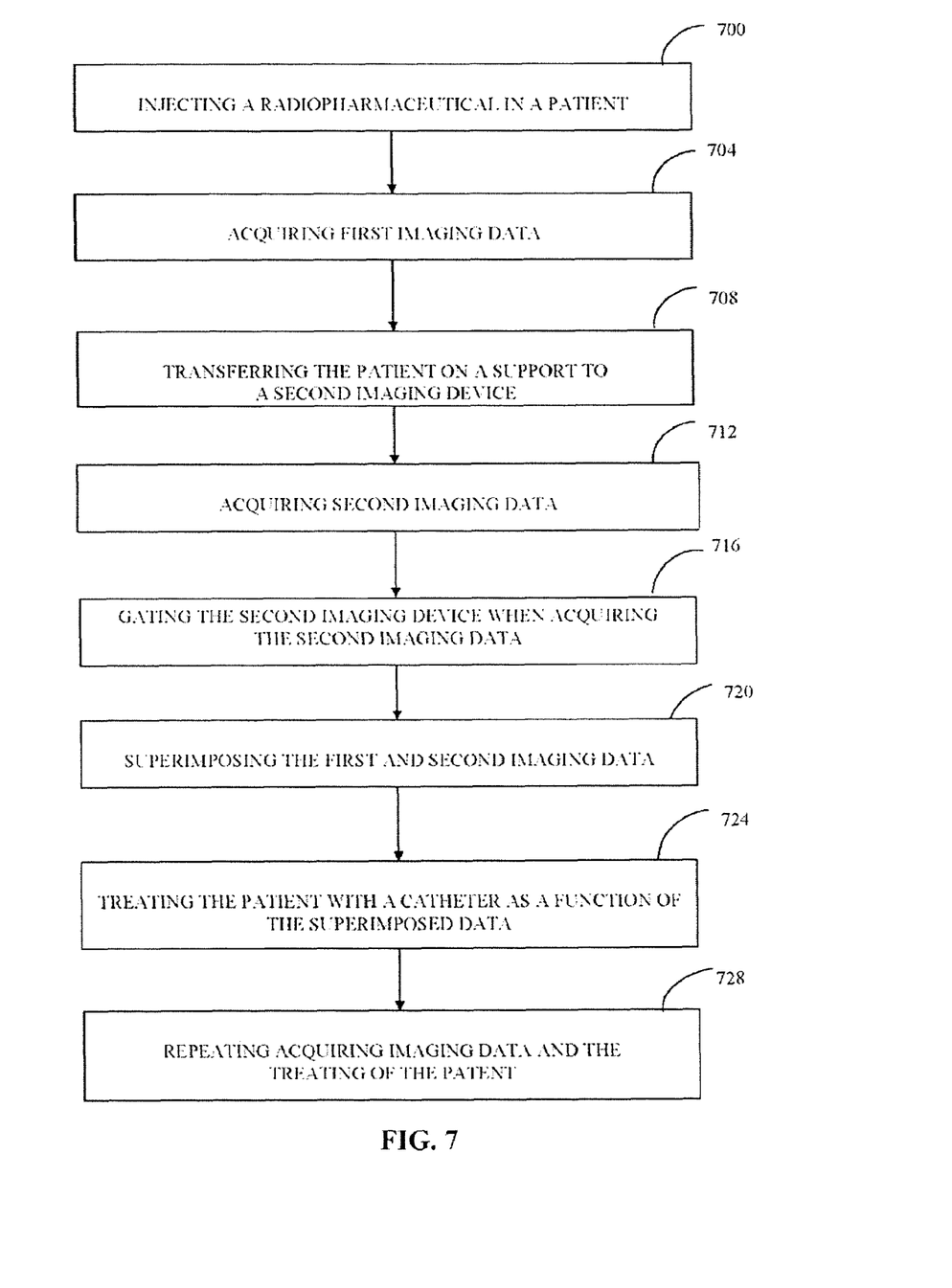
FIG. 7 is a flowchart illustrating one embodiment of a method for treating a patient using a hybrid imaging system, such as the diagnosis device of FIG. 1.

FIG. 7 shows one embodiment of a method for treating a patient using the hybrid imaging system or diagnosis device 1. For example, the hybrid imaging system or diagnosis device 1 is used for treating scar tissue in the heart as a result of a tachycardia or heart attack. Fewer or more acts may be provided. The patient 5 is positioned on the support 7. In act 700, the patient is injected with a radiopharmaceutical. For example, for a SPECT examination, the tracers Tc99m-MDP (Tc=Technetium), TI-201, or Tc99m are used. For a PET examination, flourdeoxyglucose ("FDG") is utilized. Any other known or future radiopharmaceutical for a nuclear medicine examination may be used.

In act 704, first imaging data is acquired from the patient 5 using a first imaging device, such as the imaging device 3. For example, the first imaging device is a nuclear medicine imager, such as a SPECT or PET imager as described above. The first imaging data includes imaging data operable to identify electrophysiological activity or the lack thereof. For example, the first imaging data is acquired to identify scar tissue, such as scar tissue in the heart of the patient 5.

After the first imaging data is acquired, the patient 5 is transferred to a second imaging device, such as the imaging device 4, in act 708. The patient is transferred on the support 7. For example, an automated belt or conveying system moves the patient from the first imaging device to the second imaging device without disturbing the resting position of the patient 5. The second imaging device is an imaging device structurally allowing for catheter treatment in the patient during imaging acquisition, such as a non-encapsulating imager. For example, the second imaging device is a C-arm x-ray or CT system as described above.

In act 712, second imaging data is acquired from the patient 5 using the second imaging device. The second imaging data includes anatomical imaging data, such as x-ray or CT heart images. In act 716, the second imaging device is gated with an ECG system, as described above. Gating allows for appropriate correlation of images representing a dynamic organ such as the heart. Additional components may be used for integrated or separate imaging such as the movement sensors, catheter localization systems, and imaging catheters described above.

In act 720, the first imaging data and the second imaging data are fused or superimposed. The superimposition or fusion is a two step approach. More or less steps may be involved. First, there is registration. During the registration, the image from the first imaging device and the image from the second imaging device are transferred into a common coordinate system, usually with the help of anatomical landmarks or artificial landmarks (fiducals). The second step is the so called visualization. In this step, the image points of the image data from the first imaging device and the image data from the second imaging device are mixed together by a mathematical algorithm. If there are monochrome images, the average value of the gray values a calculated. In more complex algorithms, the image data of the first and second imaging devices are allocated different weighted averages. The fusion or superimposition is accomplished by using the components described above. Any known or future technique for image data fusion, correlation, and/or superimposition may be used. Superimposing or fusing the first imaging data and the second imaging data occurs substantially at the same time as acquiring the second imaging data. By superimposing the image data, a good functional image is combined with good anatomical image. Therefore, for example, a physician or medical professional is able to accurately identify scar tissue in the heart during a medical procedure.

While second imaging data is being acquired from the patient 5, the patient 5 is resting at the second imaging device. The patient 5 is prepared for invasive catheter treatment using medical tools and medicine. In act 724, the patient 5 is treated with a catheter as a function of the superimposed data while second imaging data that is being superimposed with the first imaging data is being acquired. For example, detailed scar tissue information is provided on a detailed image of the heart to allow a physician to perform catheter ablation therapy. Substantially real time X-ray or CT data combined with the previously acquired nuclear medicine image data allows a physician to remove, cut, or interrupt unwanted electrical channels formed close to scar tissue in the heart of the patient 5.

In act 728, the imaging and treating acts are repeated. For example, the patient 5 is transferred back to the first imaging device on the support. Third imaging data is acquired from the patient 5 using the first imaging device. This allows the physician to obtain a better and more accurate image of the scar tissue. After obtaining the updated functional or scar tissue data, the patient is transferred on the support to the second imaging device. Fourth imaging data is acquired from the patient 5 using the second imaging device. The third imaging data and the fourth imaging data is superimposed, as described above, and the patient is treated with the catheter as a function of the superimposed third and fourth imaging data while acquiring the fourth imaging data. This way, unwanted electrical channels formed close to the scar tissue can be removed in a more precise manner. Imaging at different imaging devices or imagers and treating the patient can be repeated any number of times.

Additionally, instructions executable by a processor of the hybrid imaging system or diagnosis device 1 are stored in a computer-readable medium. The instructions implement the methods, acts, and processes described above. The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Also, any of the features, methods, techniques described may be mixed and matched to create different systems and methodologies.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for treating a patient using a hybrid imaging system, the method comprising:
    acquiring first imaging data from a patient using a first imaging device, the first imaging device comprising a single photon emission computed tomography system;
    transferring the patient on a support to a second imaging device, the support extending between the first imaging device and the second imaging device and the second imaging device comprising a C-arm x-ray or computed tomography system controlled by a robot unit;
    acquiring second imaging data from the patient using the second imaging device, wherein the second imaging device structurally allows for catheter treatment in the patient during acquisition of the second imaging data;
    superimposing or fusing the first imaging data and the second imaging data; and
    treating the patient with a catheter as a function of the superimposed or fused data while acquiring the second imaging data.

2. The method of claim 1, wherein the first imaging data comprises imaging data operable to identify electrophysiological activity.

3. The method of claim 1, wherein the second imaging data comprises anatomical imaging data.

4. The method of claim 1, wherein transferring the patient comprises moving the patient in a resting position by an automated process.

5. The method of claim 1, further comprising: gating the second imaging device with an electrocardiogram system when acquiring the second imaging data.

6. The method of claim 5, further comprising: measuring an electrocardiogram (ECG) to detect organ movements, the measurement results being taken into account during the gating to eliminate artifacts.

7. The method of claim 1, further comprising: injecting a radiopharmaceutical in the patient before acquiring the first imaging data.

8. The method of claim 1, wherein treating the patient with the catheter comprises treating the patient with catheter ablation therapy.

9. The method of claim 8, wherein treating the patient comprises cutting or interrupting electrical channels in the heart of the patient.

10. The method of claim 1, further comprising:
    transferring the patient on the support from the second imaging device to the first imaging device;
    acquiring third imaging data from the patient using the first imaging device;
    transferring the patient on the support to the second imaging device after acquiring the third imaging data;
    acquiring fourth imaging data from the patient using the second imaging device;
    superimposing or fusing the third imaging data and the fourth imaging data; and
    treating the patient with the catheter as a function of the superimposed or fused third and fourth imaging data while acquiring the fourth imaging data.

11. In a computer-readable medium having stored therein instructions executable by a processor, the instructions comprising:
    acquiring first imaging data from a patient using a nuclear medicine imager, the nuclear medicine imager comprising a single photon emission computed tomography system;
    transferring the patient on an automated support to a non-encapsulating imager controlled by a robot unit, the automated support extendable between the nuclear medicine imager and the non-encapsulating imager;
    acquiring second imaging data from the patient using the non-encapsulating imager; and
    superimposing or fusing the first imaging data and the second imaging data substantially at the same time as acquiring the second imaging data.

12. The instructions of claim 11, wherein the non-encapsulating imager comprises a radiographic imaging system.

13. The instructions of claim 11, wherein the nuclear medicine imager comprises a single photon emission computed tomography system or a positron emission tomography system.

14. The instructions of claim 11, wherein the non-encapsulating imager comprises a C-arm x-ray or computed tomography system.

15. The instructions of claim 11, further comprising: gating the non-encapsulating imager with an electrocardiogram system when acquiring the second imaging data.

16. The instructions of claim 11, further comprising:
    transferring the patient on the automated support from the non-encapsulating imager to the nuclear medicine imager;

acquiring third imaging data from the patient using the nuclear medicine imager;

transferring the patient on the automated support to the non-encapsulating imager after acquiring the third imaging data;

acquiring fourth imaging data from the patient using the non-encapsulating imager;

superimposing or fusing the third imaging data and the fourth imaging data substantially at the same time as acquiring the fourth imaging data.

17. A method for treating a patient using a hybrid imaging system, the method comprising:

acquiring first imaging data from a patient using a first imaging device, the first imaging device comprising a single photon emission computed tomography system;

transferring the patient on a support to a second imaging device, the support extending between the first imaging device and the second imaging device and the second imagine device comprising a C-arm x-ray or computed tomography system controlled by a robot unit;

acquiring second imaging data from the patient using the second imaging device, wherein the second imaging device structurally allows for catheter treatment in the patient during acquisition of the second imaging data including image data for soft tissue x-ray images;

superimposing or fusing the first imaging data and the second imaging data; and treating the patient with a catheter as a function of the superimposed or fused data while acquiring the second imaging data.

* * * * *

UNITED STATES PATENT AND TRADEMARK OFFICE
CERTIFICATE OF CORRECTION

| | | |
|---|---|---|
| PATENT NO. | : 7,755,058 B2 | Page 1 of 1 |
| APPLICATION NO. | : 11/862702 | |
| DATED | : July 13, 2010 | |
| INVENTOR(S) | : Michael Maschke | |

It is certified that error appears in the above-identified patent and that said Letters Patent is hereby corrected as shown below:

<u>On the Title Page</u>

Before item (74), after "*Primary Examiner*", replace "David P Porta" with --David P. Porta--.

In column 16, claim 17, line 4, before "device comprising a" replace "imagine" with --imaging--.

Signed and Sealed this
Fifth Day of April, 2011

David J. Kappos
*Director of the United States Patent and Trademark Office*